(12) United States Patent  (10) Patent No.: US 8,003,116 B2
Dobler  (45) Date of Patent: *Aug. 23, 2011

(54) FRAGRANCE SAMPLER INSERT

(75) Inventor: Sven Dobler, New York, NY (US)

(73) Assignee: Orlandi, Inc., Farmingdale, NY (US)

( * ) Notice: Subject to any disclaimer, the term of this patent is extended or adjusted under 35 U.S.C. 154(b) by 2062 days.

This patent is subject to a terminal disclaimer.

(21) Appl. No.: 10/233,136

(22) Filed: Aug. 30, 2002

(65) Prior Publication Data

US 2003/0010670 A1    Jan. 16, 2003

Related U.S. Application Data

(63) Continuation-in-part of application No. 09/858,566, filed on May 17, 2001, now Pat. No. 6,461,620, which is a continuation-in-part of application No. 09/531,296, filed on Mar. 20, 2000, now Pat. No. 6,251,408.

(51) Int. Cl.
*A61K 9/00* (2006.01)
*B65D 75/26* (2006.01)
*B65D 73/00* (2006.01)

(52) U.S. Cl. ......... 424/400; 428/905; 206/784; 206/484

(58) Field of Classification Search .................. 424/400; 428/905; 206/484, 784
See application file for complete search history.

(56) References Cited

U.S. PATENT DOCUMENTS

| | | | |
|---|---|---|---|
| 4,155,500 A | 5/1979 | Dutcher | |
| 4,208,012 A | 6/1980 | Dutcher | |
| 4,279,373 A | 7/1981 | Montealegre | |
| 4,280,649 A | 7/1981 | Montealegre | |
| 4,301,095 A | 11/1981 | Mettler et al. | |
| 4,427,111 A * | 1/1984 | Laipply | 206/210 |
| 4,484,768 A | 11/1984 | Norfleet | |
| 4,487,801 A | 12/1984 | Turnbull et al. | |
| 4,493,869 A | 1/1985 | Sweeny et al. | |
| 4,615,486 A | 10/1986 | Konicek | |
| 4,619,383 A | 10/1986 | Konicek | |
| 4,661,388 A | 4/1987 | Charbonneau | |
| 4,720,423 A | 1/1988 | Fraser | |
| 4,751,934 A | 6/1988 | Moir et al. | |
| 4,809,912 A | 3/1989 | Santini | |
| 4,848,378 A | 7/1989 | Moir et al. | |
| 4,858,831 A | 8/1989 | Spector | |
| 4,869,407 A | 9/1989 | Booth, Jr. et al. | |
| 4,880,690 A | 11/1989 | Szycher et al. | |
| 5,093,182 A | 3/1992 | Ross | |
| 5,161,688 A | 11/1992 | Muchin | |
| 5,192,380 A | 3/1993 | Hanada et al. | |
| 5,192,386 A | 3/1993 | Moir et al. | |
| 5,249,676 A | 10/1993 | Ashcraft et al. | |
| 5,391,420 A | 2/1995 | Bootman et al. | |
| 5,562,112 A | 10/1996 | Gunderman et al. | |
| 5,566,693 A | 10/1996 | Gunderman et al. | |
| 5,616,337 A * | 4/1997 | Kasianovitz et al. | 424/414 |

(Continued)

*Primary Examiner* — Blessing Fubara
(74) *Attorney, Agent, or Firm* — Paul M. Denk

(57) ABSTRACT

A fragrance sample is provided which is made from two plies (a bottom ply and a top ply) of material. A cosmetic (such as a wet fragrance) sample is deposited on the bottom ply. A wall is formed in at least one of the plies and is sized and shaped to surround the sample. The two plies are then adhered together to form a liquid tight seal between the two plies. The bottom ply can be provided with a flow barrier to impede the flow of the sample-on the bottom ply.

7 Claims, 6 Drawing Sheets

U.S. PATENT DOCUMENTS

| | | | | |
|---|---|---|---|---|
| 5,622,263 A * | 4/1997 | Greenland | | 206/581 |
| 5,645,161 A | 7/1997 | Whitaker et al. | | |
| 5,690,130 A | 11/1997 | Gunderman et al. | | |
| 5,845,847 A | 12/1998 | Martin et al. | | |
| 5,899,382 A | 5/1999 | Hayes et al. | | |
| 6,012,643 A | 1/2000 | Barlow et al. | | |
| 6,251,408 B1 * | 6/2001 | Dobler | | 424/400 |
| 6,461,620 B2 * | 10/2002 | Dobler | | 424/400 |

* cited by examiner

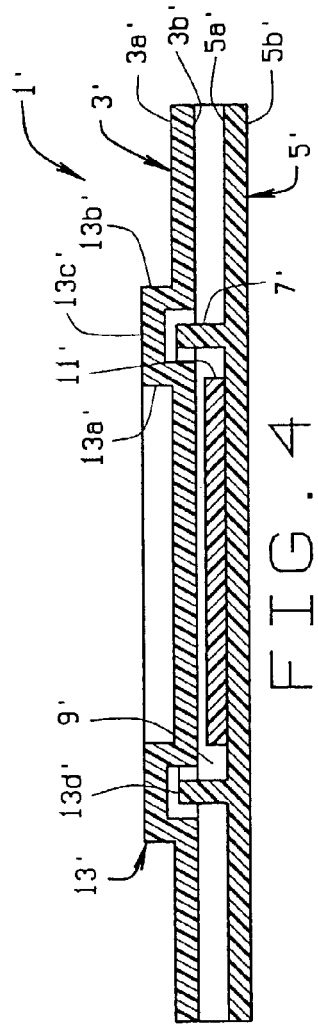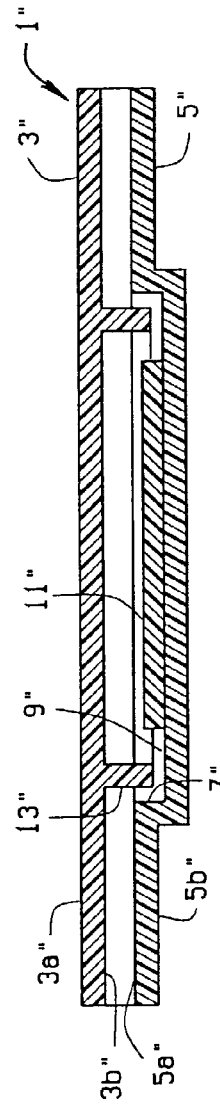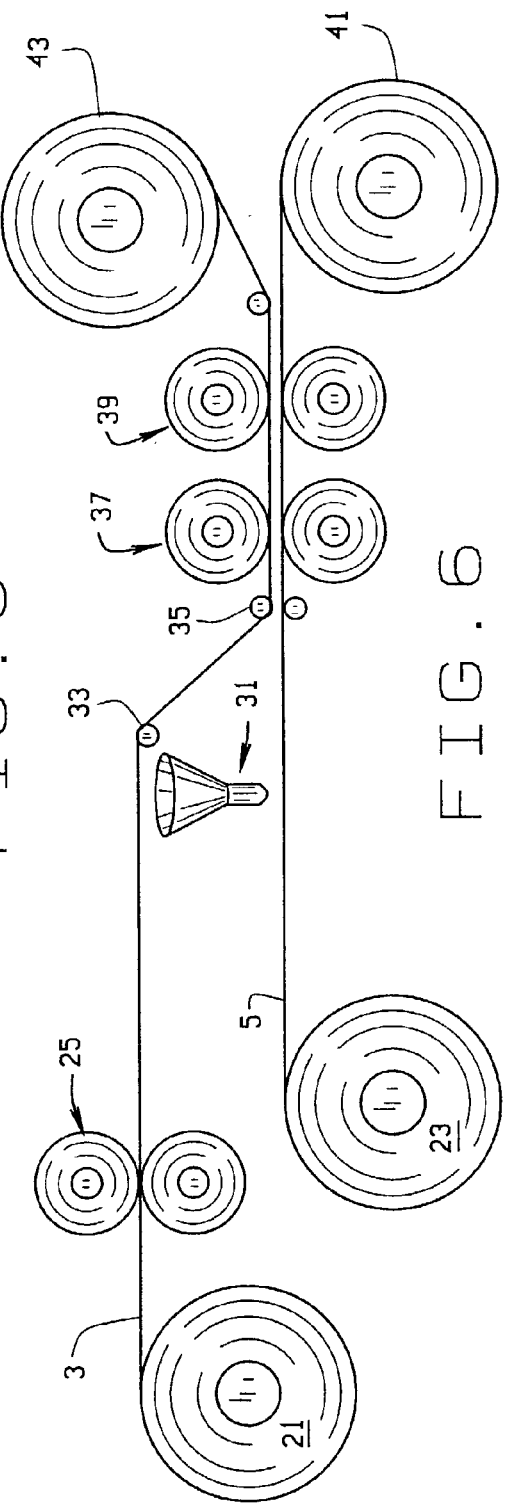

FRAGRANCE SAMPLER INSERT

CROSS-REFERENCE TO RELATED APPLICATIONS

This is a continuation-in-part of application Ser. No. 09/858,566, filed May 17, 2001, now U.S. Pat. No. 6,461,620, which, in turn, is a continuation-in-part of application Ser. No. 09/531,296, filed Mar. 20, 2000, now U.S. Pat. No. 6,251,408, both of which are entitled Fragrance Sampler Insert, and both of which are incorporated herein by reference.

BACKGROUND OF THE INVENTION

This invention relates to fragrance samplers which are inserted in magazines or used in direct mailings.

Traditionally fragrance samplers were dry pre-scented blotter cards that had to be individually overwrapped to contain the fragrance for use in direct mail or magazine advertising. Beginning in the late 1970's, the micro-encapsulated Scentstrip® style magazine and direct mail insert was introduced. The Scentstrip insert is described in U.S. Pat. No. 5,093,182 to Ross. This product was produced on wide web offset printing equipment and therefore offered significant cost efficiencies for mass marketing. However, this was still a dry sample since the water moisture in the deposited fragrance slurry would very quickly wick into the paper substrate and leave the product sample dry. In fact, the entire technology depended on this moisture wicking since the wet microcapsules would not bond to the paper and would not break upon opening of the sampler. The microcapsules only break and release the fragrance oil when they are dry and are bonded to the paper. The draw back with this product was that it did not replicate the actual wet perfume product very well. In order to sample the fragrances in its real life wet form, the moisture wicking of the wet fragrance slurry deposited in the wide web offset printing process needed to be prevented. This was most easily accomplished by using existing narrow web flexographic label printing technology to create a pressure sensitive product that incorporated a wet fragrance or cosmetic sample material between impervious barrier materials such as plastic films and foil structures.

Currently there are three main fragrance sampler patents that guide us in wet fragrance or cosmetic sampling in magazines and direct mail. One is U.S. Pat. No. 5,391,420 to Bootman, which describes a pressure sensitive label comprising two plies of a film or plastic material: one bottom pressure sensitive ply, a deposit of fragrance material and an overlay of a second ply which traps said fragrance deposit. The sealing is by heat seal. The draw back of this product is that the fragrance material is often forced into and through the seal areas under pressure from the stacking forces of many magazines or inserts in distribution.

U.S. Pat. No. 5,161,688 to Muchin perfects upon the Bootman product by introducing a center ply material which has a die-cut window. This window ply is introduced onto the bottom pressure sensitive ply and thus creates a well for the fragrance material. The top, third ply is then added and the result is that stacking forces are distributed on to the widow ply and the fragrance material is exposed to less forces that may lead to seal failures and leakage: a major defect in the original product.

A modification of this second patent concept is described in U.S. Pat. No. 5,622,263 to Greenland. Greenland uses a liquid polyethylene or other hot liquid plastic material that creates the above-mentioned well and also assists in the heat sealing process. The draw back of the Muchin patent is that the additional window ply involves additional cost and manufacturing complications for die-cutting and introducing the third ply in the process. The Greenland concept also adds additional material cost and slows the process as the liquid plastic material needs to be deposited and bonded to the top and bottom ply. Further, the hot liquid plastic material introduces foreign odor and can, in some circumstances, contaminate the cosmetic or fragrance sampling material.

There are various other patents that deal with cosmetic sampling. Gunderman (U.S. Pat. No. 5,690,130) discloses a sampling device with a unit dose of cosmetic that is screen printed onto a base paper with a perimeter adhesive and clear film overlay. In this case a well area is embossed to receive an integral applicator. The well is not designed as a receptor for the cosmetic product nor is the embossing incorporated into the seal so as to afford strength and allow the seal to withstand pressure better. Also, this sampler uses screen printing and, as disclosed, is not intended or capable of delivering a wet liquid dose of cosmetic material. Lastly, a pressure sensitive base material is not envisioned which would allow automatic affixing as a label onto magazine or direct mail materials as the current Invention envisions.

Gunderman (U.S. Pat. No. 5,566,693) describes a screen printed sampler that delivers a cosmetic dose under a clear film overlay with pressure sensitive base material allowing affixing as a label. Again, this sampler is not designed to deliver a wet fragrance. The fragrance formulation requires fragrance to be mixed in a powder-based vehicle so that it can be screen printed. Also the sealing is not designed to contain wet fragrance or provide enough strength to contain liquid under stacking pressure. Further no embossing is envisioned to hold a cosmetic dose or to create seal wall integrity. Gunderman (U.S. Pat. No. 5,562,112) envisions a lipstick sampler, again with neither a well or an embossed seal wall feature.

Ashcraft (U.S. Pat. No. 5,249,676) describes a multi-layer film with a flavor carrier layer between barrier layers. This does not create a wet fragrance sampler and there is no provision to create seals by embossing or otherwise that will allow a wet cosmetic sample to be contained under pressure.

Moir (U.S. Pat. No. 5,192,386) describes a screen printed, two-ply sampler with perimeter adhesive and clear film overlay. The cosmetic ingredient is a cosmetic powder, a heated oily, non-liquid waxy material, or a fragrance in a dry powder formulation. The product is dry, not wet, and there is no provision for creating heat sealed, embossed or interlocking walls to define a well and create internal seal strength sufficient to withstand stacking forces.

Szycher et al. (U.S. Pat. No. 4,880,690) shows a perfume patch.

Moir (U.S. Pat. No. 4,848,378) discloses a cosmetic screen printed, two-ply sampler that allows a pattern deposit of the cosmetic ingredient in the form of a non-smeary powder. This product is not pressure sensitive has no embossed wells or seal walls and does not deliver a wet sample.

Dreger (U.S. Pat. No. 4,769,264) discloses a label product comprising at least two sheets, bonded by adhesive, with microencapsulated fragrance. The liquid fragrance inside the microspheres is so little that it does not create a wet rendering of the product and is as dry to the touch and in current day dry "scents/rips". There is no mention of creating a well to hold the cosmetic dose in a confined area, nor is any use made of embossing or interlocking seal walls to create an improved seal and resist stacking pressure.

Moir (U.S. Pat. No. 4,751,934) discloses another version of a screen printed cosmetic powder formulation that may include fragrance in a two-ply pressure sensitive label construction. The seals of the two ply layers are by adhesive seal and the product rendering is dry or waxy, as in the lipstick dose version, but not wet as contemplated in the current invention. No embossing or debossing is used to create well areas or build wall seals.

Fraser (U.S. Pat. No. 4,720,423) describes using in a multilayer strip having an adhesive with frangible microcapsules as a package overwrap. This product does not render a wet sample and create wells or seal walls either.

Charbonneau (U.S. Patent NQ. 4,606,956) discloses a pressure sensitive two ply label construction with conventional microencapsulated slurry applied wet and then allowed to dry as is the conventional practice in the manufacture of scent strips. The product sample is rendered in a dry state, no wells or embossed walls are used to create a more impervious seal that can hold up to stacking forces.

There are several other patents that disclose fragrance samplers. Charbonneau (U.S. Pat. No. 4,606,956) shows an on page fragrance sampling device. Charbonneau (U.S. Pat. No. 4,661,388) shows a pad fragrance sampling device. Fraser (U.S. Pat. No. 4,720,423) shows a package opening system. Moir et al. (U.S. Pat. No. 4,751,934) discloses a cosmetic sampler. Dreger (U.S. Pat. No. 4,769,264) discloses an on page fragrance sampling device. Moir et al. (U.S. Pat. No. 4,848,378) discloses a cosmetic sampler. Moir et al. (U.S. Pat. No. 5,192,386) discloses a method of making a cosmetic sampler. Ashcraft et al. (U.S. Pat. No 5,149,676) discloses a flavor burst structure and method of making it. Gundermann (U.S. Pat. No. 5,562,112) discloses a lipstick sampler. Gundermann (U.S. Pat. No. 5,566,693) discloses a fragrance sampler. Gundermann (U.S. Pat. No. 5,690,130) discloses a cosmetic sampler with an integrated applicator. Sweeny (U.S. Pat. No. 4,493,869) discloses fragrance microcapsules clear substrate. Turnbull (U.S. Pat. No. 4,487,801) discloses a fragrance releasing pull-apart sheet. Greenland (U.S. Pat. No. 5,622,263) discloses a sampler package and method of making it. Muchin (U.S. Pat. No. 5,161,688) discloses a sampler and method of making the sampler. Bootman (U.S. Pat. No. 5,391,420) discloses fragrance laden pouch samplers.

BRIEF SUMMARY OF THE INVENTION

Briefly stated, a sampler is provided for insertion into an article such as a magazine or a mass mailing. The sampler includes a bottom ply and a top ply, both of which have an upper surface and a lower surface. A wall formed in at least one of the top and bottom plies to define an area which surrounds the sample. If the wall is formed in the bottom ply, the wall defines a well which receives the sample. A cosmetic sample (such as a wet fragrance sample) is deposited on the bottom ply. The top ply and bottom ply are adhered together to form a seal to substantially prevent leakage of the sample. A barrier formation can be formed in the bottom ply. The barrier formation is positioned to be within the area defined by the wall and is sized and shaped to impede the flow of said sample on said bottom ply. For example, the barrier formation can comprise a plurality of dimples, knurls, baffles, or grooves.

BRIEF DESCRIPTION OF THE SEVERAL VIEWS OF THE DRAWINGS

FIG. 4 is a cross-sectional view of an alternative construction of the fragrance sampler;

FIG. 5 is a cross-sectional view of another alternative construction of the fragrance sampler;

FIG. 6 schematic drawing of an alternative process for producing the sample of either FIG. 2 or 4;

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

Figure 1:
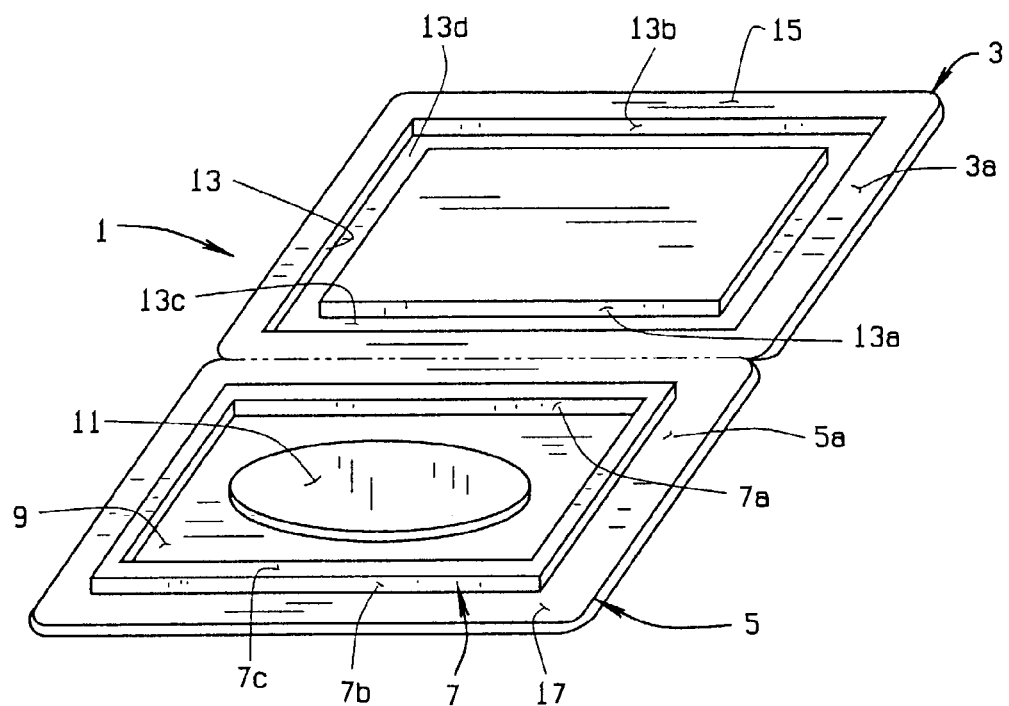
FIG. 1 is a perspective view of a fragrance sampler of the present invention prior to assembly of the sampler.
Figure 2:
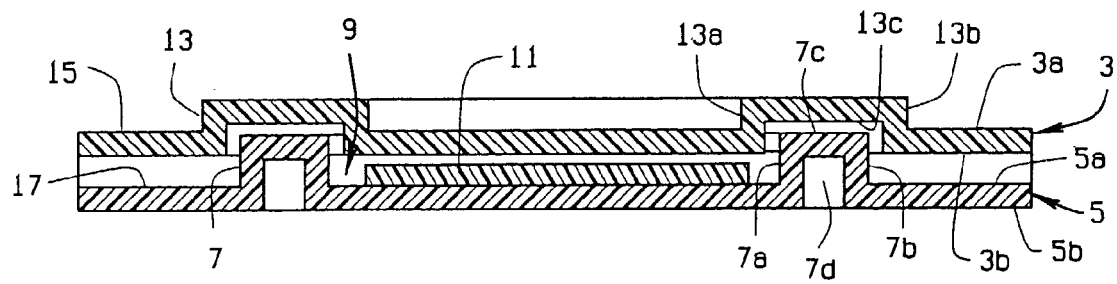
FIG. 2 a cross-sectional view of the sampler when assembled.

A first embodiment of a sampler 1 of the present invention is shown in FIGS. 1 and 2. The sampler 1 includes a top ply 3 and a bottom ply 5, both of which are preferably formed from a foil, a polyester, or a polyethylene laminated structure. The plies can alternatively be made of an acetate or other paper, foil, and plastic film laminated or non laminated barrier plies. To facilitate affixing the sampler, for example, in a magazine or other publication, a pressure sensitive adhesive can be applied to either the top ply 3 or bottom ply 5 of the sampler.

The top and bottom plies 3 and 5 each include top and bottom surfaces 3a, 5a and 3b, 5b. A wall 7 is formed in the bottom ply 5 which extends up from the bottom ply's upper surface 5a. The wall 7, as shown, has an inner surface 7a, an outer surface 7b, and a top surface 7c which define a channel 7d in the bottom ply bottom surface 5b. The channel 7d is preferably rectangular in cross-section (but could have other configurations), and the wall 7 defines a "double wall." The wall 7 also defines a well 9 into which a wet fragrance sample 11 can be deposited. The fragrance sample 11 can be a sample of a perfume, or a cosmetic creme, lotion, hair color tint, lip stick, powder, or other cosmetic ingredient.

An opposing wall 13 is formed in the top ply 3 and extends upwardly from the top ply top surface 3a (with reference to FIG. 2). The wall 13 has an inner surface 13a, an outer surface 13b, and a top surface 13c which, in combination, define a channel 13d in the top ply bottom surface 3b (again, with reference to FIG. 2). The top ply channel 13d corresponds in shape to the bottom ply wall 7. As with the bottom ply channel 7d, the top ply channel 13d is preferably rectangular in cross-section (but could have other configurations that correspond to the configuration of the bottom ply channel 7d), and the wall 13 is a "double wall." As seen in FIG. 2, the wall 13 in the upper ply has dimensions slightly larger than the dimensions of the bottom ply wall 7, and the channel 13d is slightly wider than the channel 7d. Thus, the top ply wall 13 receives the bottom ply wall 7, as seen in FIG. 2, so that the walls 7a-c defining the lower ply channel 7d are substantially adjacent the walls 13a-c defining the upper ply channel 13d.

The top and bottom ply walls 7 and 13 are preferably formed by an embossing/debossing process.

As can be seen in FIGS. 1 and 2, when the walls 7 and 13 are formed, the top and bottom plies each include a frame 15, 17 surrounding the walls 7 and 13, respectively. The top ply 3 and bottom ply 5 are adhered together to cover and close the well 9 so that the sample 11 will be sealed in the well 9 between the two plies. The plies can be joined by heat sealing the two plies together or using an adhesive to bond the top plies together. If an adhesive is used, the adhesive can be cationic cure coating adhesive, or other equally acceptable adhesive which will form a liquid tight barrier to prevent premature release of the fragrance contained in the well 9.

Although the walls 7 and 13 are shown in FIGS. 1 and 2 to be "double walls" with one wall being received in the channel of the other, one of the walls 7 and 13 could alternatively be formed as single walls as seen in the sampler 1' of FIG. 4. The sampler 1' includes a top ply 3' and a bottom ply 5'. The top and bottom plies 3' and 5' each include top and bottom surfaces $3a'$, $5a'$ and $3b'$, $5b'$. A wall 7' extends up from the bottom ply's upper surface $5a'$. Unlike the wall 7 of the sampler 1 of FIGS. 1 and 2, the wall 7' is a single wall. The wall 7' is spaced inwardly from the outer edge of the sampler bottom ply 5' and extends around the bottom ply 5' to form a well 9' into which a wet fragrance sample 11' can be deposited.

An opposing wall 13' extends up from the top ply top surface $3a'$. The wall 13' has an inner surface $13a'$, an outer surface $13b'$, and a top surface $13c'$ which, in combination, define a channel $13d'$ in the top ply bottom surface $3b'$. The top ply channel $13d'$ is sized to receive the bottom ply wall 7', so that the walls 7' and 13' are engaged when the sampler 1' is formed.

Another alternative construction for the fragrance sampler is shown in FIG. 5. In this construction, the sampler 1" includes a top ply 3" and a bottom ply 5" having upper and lower surfaces $3a''$, $5a''$ and $3b''$, $5b''$, respectively. Unlike the embodiments of FIGS. 1 and 4, the fragrance sampler 1" includes a well 9" formed in the bottom ply 5" which holds the fragrance sample 11". The well 9" can be formed by either an embossing or debossing process. The top ply 3" includes a wall 13" which extends from the top ply bottom surface $3b''$. The wall 13" is sized to be received in the well 9" so that, when the sampler 1" is formed, the wall 13" will be adjacent the wall 7" of the well 9" and so that the two walls will engage each other to form a liquid tight seal to retain the liquid fragrance sample in the well 9". Unlike the samplers 1 and 1' of FIGS. 1-4, the sampler 1' includes no "double walls", rather, both the walls 7" and 13" are single walls.

Figure 3:
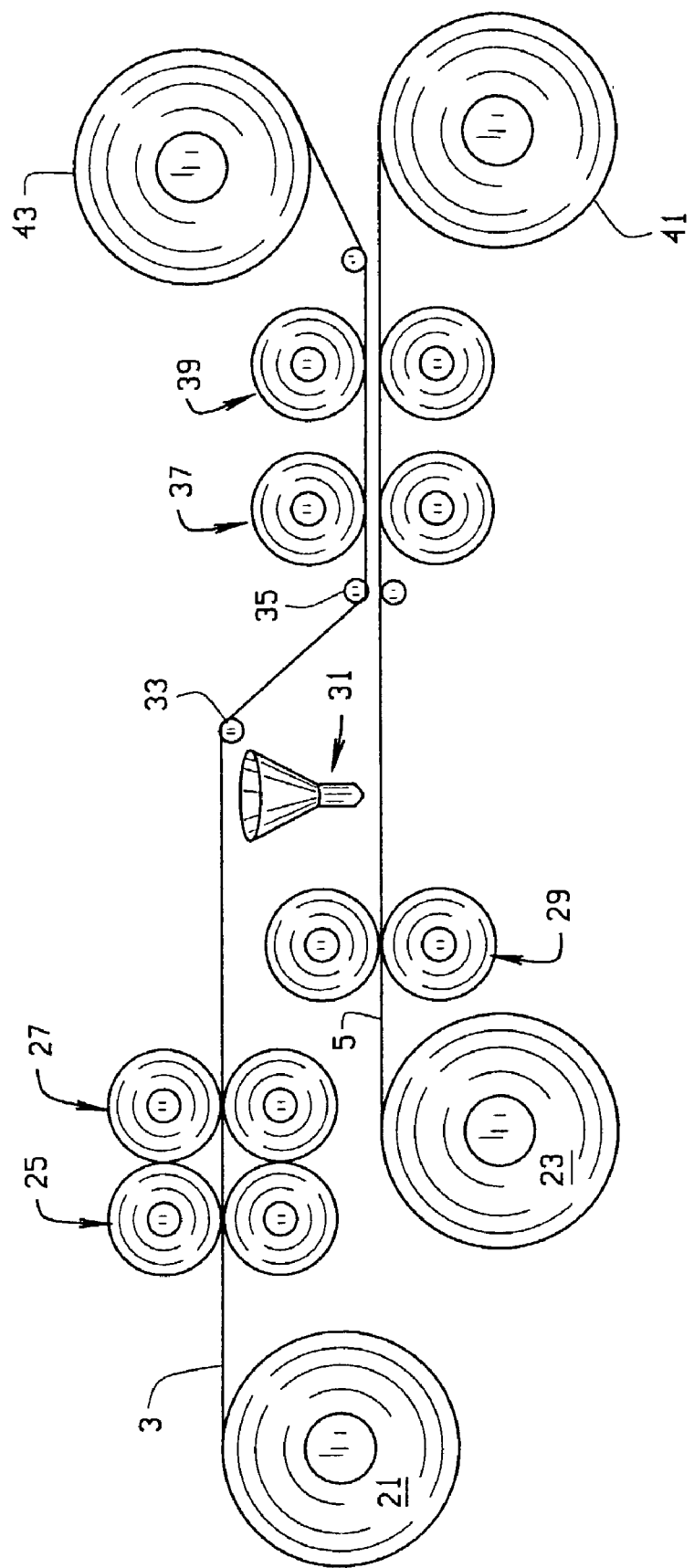
FIG. 3 is a schematic drawing of the sampler producing process.

The process for producing the samplers 1, 1', and 1" is shown schematically in FIG. 3. Webs of the top and bottom ply material are originally contained on rollers 21 and 23, respectively. The top ply material is pulled off the top ply roller 21 and passed through a printer station 25 and then through an embossing station 27. At the printer station 25 desired graphics are printed on the top surface $3a$, $3a'$, $3a''$ of the top ply 3, 3', 3". The top ply wall 13, 13', 13" is formed at the embossing station 27. The top foil laminated ply is printed on a narrow web flexographic or letter press printing press, with all subsequent finishing steps performed either in-line or off-line.

While the top ply is being processed, the bottom ply material is pulled off the bottom ply roller 23 and passed through an embossing station 29 where the bottom ply wall 7, 7', 7" is formed. A flat bed embossing tool is used to push up or emboss the wall 7, 7', 7" on the bottom ply to form the well 9, 9', 9". The bottom ply embossing can be also be formed by rotary embossing methods.

The bottom ply 5, 5', 5" is passed under an injection station 31 where a liquid fragrance sample is deposited in the well 9, 9', 9". The sample 11, 11', 11" can be deposited in any other desired manner, such as extrusion, spray, flexographic equipment or silkscreen.

After the top ply has been printed and after the wall 13, 13', 13" is formed in the top ply, the top ply is passed about a pair of rollers 33 and 35 to bring the top ply 3, 3', 3" into close proximity with the bottom ply 5, 5', 5". The path of travel of the bottom ply is preferably substantially horizontal, at least after the fragrance sample has been deposited in the bottom ply well 9, 9', 9", to avoid spilling of the sample. Thus, the top ply 3, 3', 3" is preferably brought to the bottom ply 5, 5', 5". However, the process could be designed so that the bottom ply is brought up to the top ply. The two plies are then passed through a sealing station 37 where the two plies are adhered together to form a liquid tight seal which will contain the fragrance sample in the chamber. The sealing station interlocks with the well wall 7, 7', 7" with the top ply wall 13, 13', 13" to form a safe, closed well for the sample material. As can be appreciated, the webs of top ply and bottom ply material move at an indexed rate such that when the two plies are brought together at the sealing station, the top ply wall 13, 13', 13" will be in alignment with the bottom ply wall 7, 7', 7". The sealing station 37 is preferably is a heat sealer, and the top and bottom plies can be adhered or sealed together for example, by ultrasonic welding, or other standard heat sealing processes which will create a seal between the two plies. Alternatively, as noted above, the sealing station can utilize an adhesive, such as cationic cure coating adhesives, traditional cohesive seals, or adhesive seals, which will bind the top and bottom plies together to form the seal.

The joined plies are then passed to a die-cut station 39 where side portions of the frames 15 and 17 are removed from the formed samplers. The die-cutting step can be performed with either rotary or flat bed equipment. The formed samplers are then collected on a product roller 41. Product is delivered in roll form for automatic applications to other printed materials. The die-cutting station 39 can also form perforations between adjacent samplers to facilitate separation of the samplers. The waste material can be collected on a waste roller 43.

If desired, a pressure sensitive material with a release liner can be incorporated into the bottom ply so as to result in a product that can later be readily applied to another substrate using affixing equipment. Alternatively, the pressure sensitive adhesive with its release liner can be applied to the bottom layer ply. The pressure sensitive adhesive can be applied to the bottom ply either as a pretreatment or after the embossing/debossing process.

An alternative production process is shown in FIG. 6. As with the process of FIG. 3, webs of the top and bottom ply material are originally contained on rollers 21 and 23, respectively. The top ply material is pulled off the top ply roller 21 and passed through a printer station 25 where desired graphics are printed on the top surface of the top ply. At the same time, the bottom ply material is pulled off the bottom ply roller 23 under an injection station 31 where a liquid fragrance sample is deposited on the bottom ply. As can be appreciated, in this version, the liquid fragrance sample is deposited on the bottom ply prior to the formation of the walls of the top and bottom plies.

After the top ply has been printed, the top ply is passed about a pair of rollers 33 and 35 to bring the top ply into close proximity with the bottom ply. The path of travel of the bottom ply is preferably substantially horizontal, at least after the fragrance sample has been deposited on the bottom ply to avoid spilling of the sample. Thus, the top ply is preferably brought to the bottom ply. However, the process could be designed so that the bottom ply is brought up to the top ply. The two plies are then passed through a sealing station 37. At the sealing station 37, the walls of the top and bottom plies are formed, and the two plies are adhered together to form a liquid tight seal which will contain the fragrance sample in the chamber. The sealing station interlocks with the well wall with the top ply wall to form a safe, closed well for the sample material. As can be appreciated, the webs of top ply and bottom ply material move at an indexed rate such that when the two plies are brought together at the sealing station, the fragrance will be within the walls formed at the sealing station and, the printing on the top ply will be above the liquid fragrance sample. The sealing station 37 is preferably is a heat sealer, which embosses/debosses the top and bottom ply walls in the sampler at the same time the sampler plies are heat sealed together.

The joined plies are then passed to a die-cut station 39 where side portions of the frames 15 and 17 are removed from the formed samplers. The die-cutting step can be performed with either rotary or flat bed equipment. The formed samplers are then collected on a product roller 41. Product is delivered in roll form for automatic applications to other printed materials. The waste material can be collected on a waste roller 43.

In another variation, the walls in the bottom ply can be can be "pre-formed" to allow for filling of the well in an off-line operation.

As can be appreciated, the sampler of the present invention is easily formed from only two plies of material. The top and bottom ply walls are substantially adjacent each other, to engage each other to form a liquid tight seal around the fragrance sample. Additionally, the adjacent walls will reinforce each other to enable the walls to carry the stacking or compression forces to reduce seal failures and fragrance leaks.

Figure 7A:
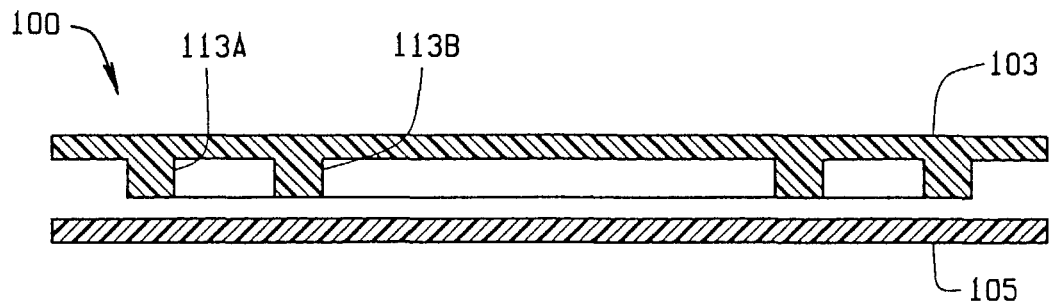
FIGS. 7A-C show three alternative constructions of the fragrance sampler which include single walls.

Several different alternative configurations of the fragrance sampler are shown in FIGS. 7A-9D. In FIG. 7A, the fragrance sampler 100 has a top ply 103 and a bottom ply 105. The bottom ply 105 is flat. That is, it does not include any walls or wells which define a chamber. Rather, the top ply has a pair of spaced apart walls 113A and 113B which are concentric with each other, and which extend downwardly from the bottom surface of the top ply. The sampler 100 is formed in substantially the same way as described above, with the fragrance sample being deposited on the bottom ply 105 in an area which will be surrounded by the wall 113B, so as to be contained within the sampler upon sealing of the sampler. As can be appreciated, the two plies can be reversed, so that the walls 113A, B form a chamber into which the fragrance sample is deposited during formation of the sampler. In this case, the well will be formed in the bottom ply, and the top ply will be flat. The top ply will then be sealed (such as by heat sealing) to the bottom ply to form a liquid tight seal between the two plies.

Figure 7B:
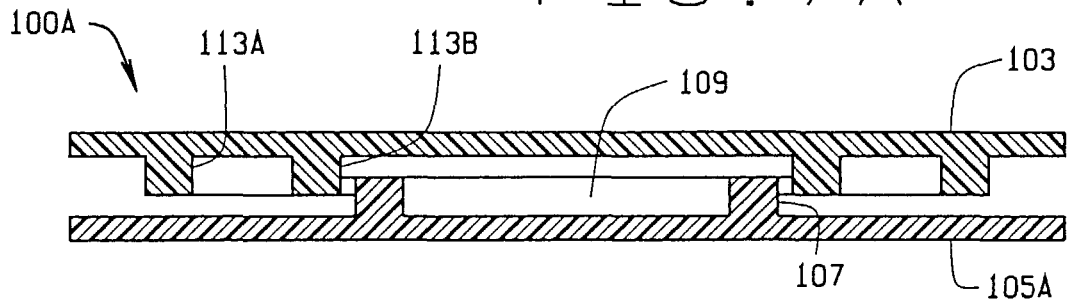

The sampler 100A shown in FIG. 7B includes the top ply 103 identical to the top ply 103 of the sampler 100 (FIG. 7A), and a bottom ply 105A. The bottom ply includes a single wall 107 which extends upwardly from the upper surface of the bottom ply to define a fragrance chamber 109. The bottom ply wall 107 is positioned to be contained within the top ply wall 113B, and sized so that its outer surface will abut the inner surface of the top ply wall 113B. Thus, the walls 107 and 113B will effectively engage each other when the sampler is sealed.

Figure 7C:
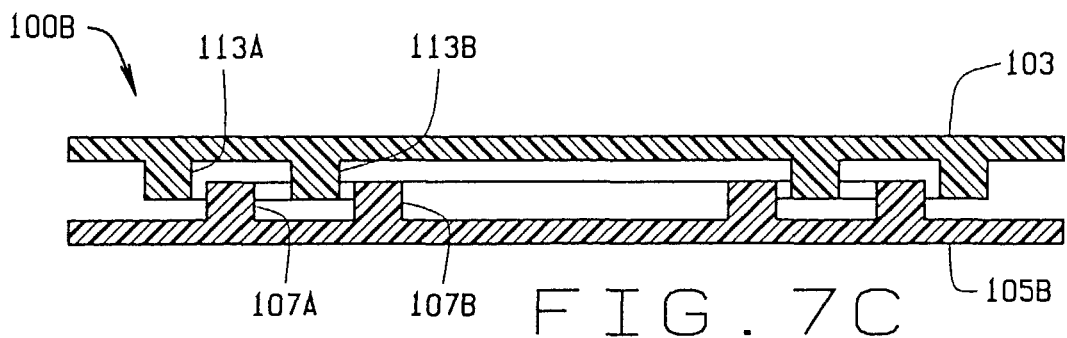

The sampler 100B shown in FIG. 7C includes the top ply 103 identical to the top ply 103 of the sampler 100 (FIG. 7A), and a bottom ply 105B. The bottom ply 105B includes a pair of spaced apart walls 107A and 107B which are concentric with each other, the wall 107B being contained within the wall 107A. As seen, the top ply walls and bottom ply walls are sized to be off-set from each other, such that the bottom ply wall 107A is received between the top ply walls 113A and 113B; and the bottom ply wall 107B is received inwardly of the top ply wall 113B. Thus, the walls 113A, B and 107A, B mesh with each other.

Figure 8A:
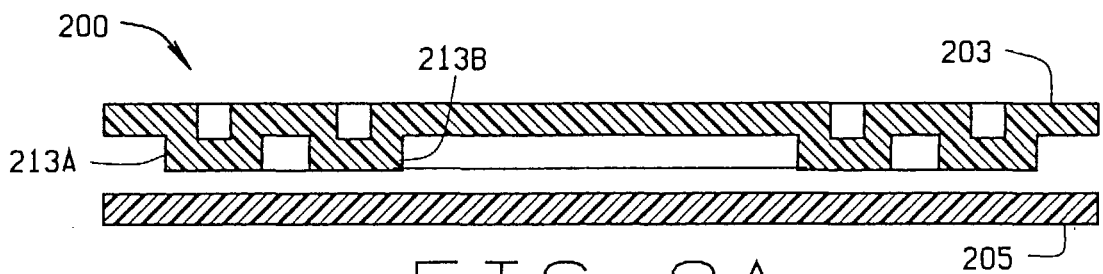
FIGS. 8A-B show two other alternative constructions of the fragrance sampler which include double walls.
Figure 8B:
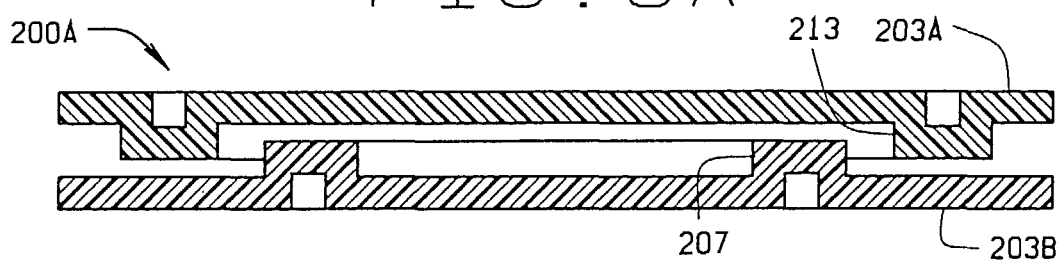

The samplers 100, 100A, and 100B all include single walls, as opposed to double walls, such as the walls 7 and 13 of the sampler 1 (FIG. 2). The samplers 200 and 200A shown in FIGS. 8A and 8B, respectively, include only double walls. The sampler 200 (FIG. 8A) includes a top ply 203 and a bottom ply 205. The bottom ply 205 is identical to the bottom ply 105 (FIG. 7A); it is flat and has no walls, wells, etc. The top ply 203 includes a pair of double walls 213A and 213B which are concentric with each other, the wall 213B being formed within the wall 213A. As seen in FIG. 8A, the concentric double walls, which are adjacent each other, give the top ply a crenelated appearance. As can be appreciated, the sampler 200 is similar to the sampler 100, except that the single top ply walls 113A, B of the sampler 100 have been replaced with the double walls 213A, B. Hence, the sampler 200 would be formed substantially the same way as the sampler 100. As with the sample 100, the sampler 200 could be formed such that the walls are formed in the bottom ply to define a well into which the sample is deposited. The top ply would then be flat. After the sample is deposited in the well, the two plies are brought together, as discussed above, to adhere the two plies together to form a liquid tight seal between the two plies.

The sampler 200A (FIG. 8B) is somewhat similar to the sampler 1 (FIG. 2). It includes a top ply 203A and a bottom ply 203B. The top ply 203A includes a double wall 213 which extends downwardly from the top ply's bottom surface. The bottom ply includes an upwardly extending wall 207. In the sampler 1 the wall 7 is received in the channel defined by the wall 13. In the sampler 200A, the respective location of the bottom ply wall has been moved relative to the top ply wall, so that the outer surface of the bottom ply wall 201 is adjacent the inner surface of the top ply wall 213 when the sampler is formed.

Figure 9A:
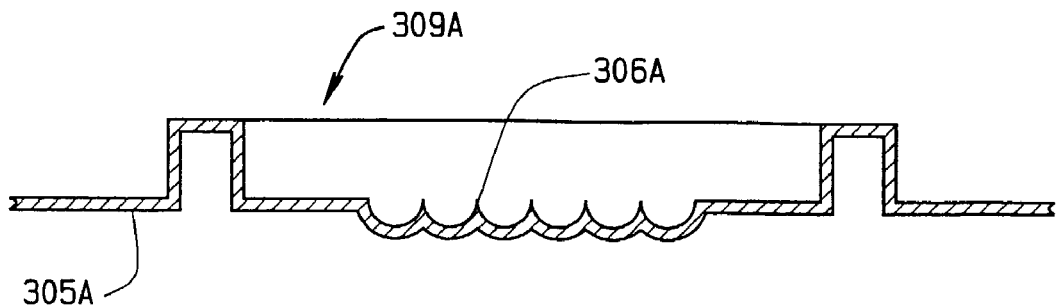
FIGS. 9A-D show alternative constructions of the sampler bottom ply, wherein the bottom ply is provided with flow barriers.
Figure 9B:
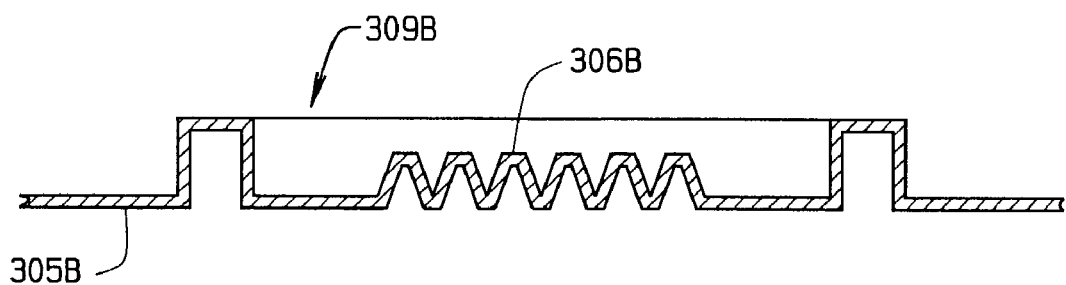
Figure 9C:
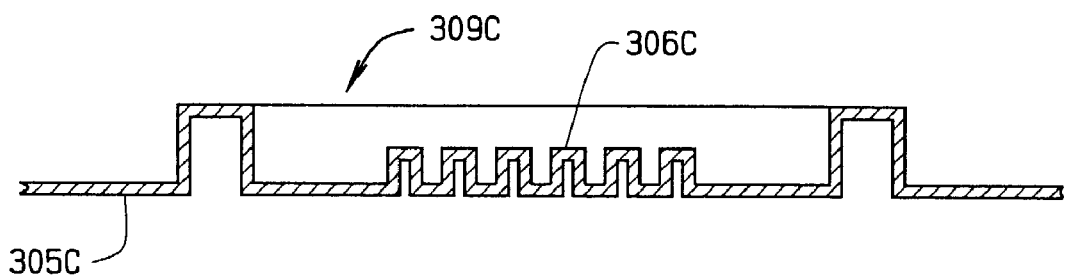
Figure 9D:
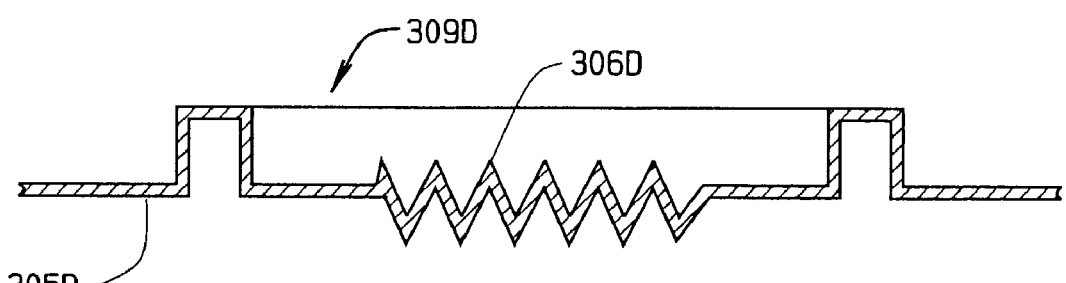

FIGS. 9A-9D show various alternative configurations to the wells 309A-D in the bottom plies 305A-D. In FIG. 9A, the well 309A is provided with a bottom surface having dimples 306A. The dimples are preferably formed in a desired pattern in the bottom of the well 309A. In FIG. 9B, the well 309B is provided with knurls 306B in the bottom surface of the well. In FIG. 9C, the well 309C is provided with baffles 306C in the form of crenellations which extend across the well. And, in FIG. 9D, the well 309D is provided with triangular grooves or hatches 306D in the bottom surface of the well. In each of the bottom plies 305A-D, the formations 306A-D in the bottom surface of the well provide barriers to the flow of the wet sample which is deposited in the well. The four formations shown are illustrative only, and other types of formations which will impede the flow of a wet sample can also be used. The barriers shown in FIGS. 9A-D can be incorporated into any of the samplers discussed above. The barriers can be formed in any desired manner, but are preferably formed in the same manner that the top and bottom ply walls are formed.

Figure 10:
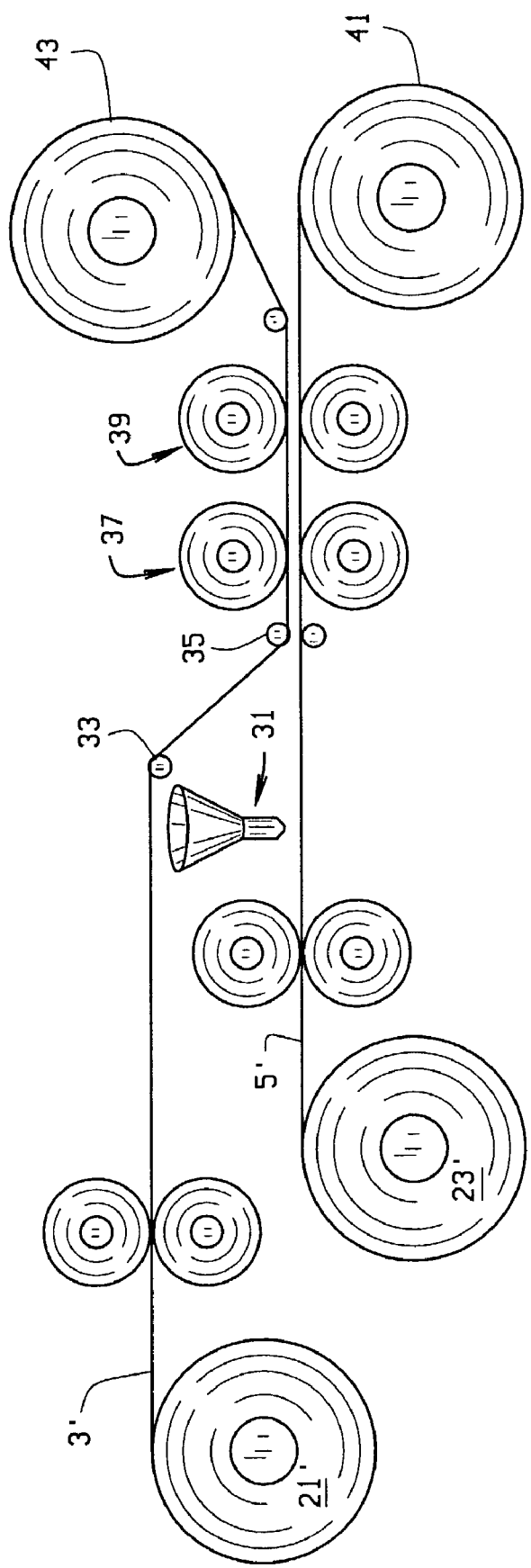
FIG. 10 is a schematic view of an alternative process for manufacturing the sampler.

FIG. 10 shows a method, somewhat similar to the method of FIG. 6, for producing the samplers. In this method, the top and bottom plies are pre-formed—that is, the various walls in the top and bottom plies are formed in a first operation to form a continuous web of sampler top and bottom plies. The two webs are formed onto rolls 21' and 23' from which the webs 3' and 5' are pulled. As can be appreciated, the two webs 3' and 5' threaded into the machinery, such that when they are brought together at the sealing station 37, the two plies will be in register. Prior to reaching the sealing station, the bottom ply 5' is brought past the injection station 31 where the sample is injected onto the ply 5'. The web 5' is threaded into the machinery so that the sample will be deposited in the well of the bottom ply (if the well is preformed). The web then passes through the cutting stating 39 where the sealed web is either perforated, or cut, to produce separable (or separated) samplers which can then be inserted in a magazine, mailer, etc.

As various changes could be made in the above constructions without departing from the scope of the invention, it is intended that all matter contained in the above description or shown in the accompanying drawings shall be interpreted as illustrative and not in a limiting sense.

The invention claimed is:

1. A sampler, for inserting into a magazine or mail piece comprising:
    a bottom ply having an upper surface, a lower surface, and a wall on said upper surface, said wall defining a well, said bottom ply upper surface having said wall formed therein and said bottom ply with said wall defining said well into which a sample is deposited;
    a cosmetic sample deposited in said well;
    a top ply having an upper surface and a lower surface, said top ply having a wall formed in the top ply lower surface, the top ply wall forming closure with the bottom ply wall, and the top ply and bottom ply being adhered together, through their walls, to form a seal to substantially prevent leakage of the cosmetic sample therefrom;
    said bottom ply further including a barrier formation in said well, inwardly of said bottom ply wall, said barrier formation being formed over a substantial surface of the upper surface of the bottom ply within the confines of its formed wall, said barrier formation being sized and shaped to impede the flow of a sample deposited upon said bottom ply, and said top ply and bottom ply and their walls being adhered together through the cooperation of their walls to form a seal to substantially prevent leakage of any sample therefrom.

2. The sampler of claim 1 wherein said barrier formation comprises a plurality of dimples.

3. The sampler of claim 1 wherein said barrier formation comprises knurls.

4. The sampler of claim 1 wherein said barrier formation comprises a plurality of baffles.

5. The sampler of claim 1 wherein said barrier formation comprises a plurality of grooves.

6. The sampler of claim 1 wherein said grooves are generally V-shaped.

7. The sampler of claim 1 wherein one of the top and bottom plies is provided with a pressure sensitive adhesive.

* * * * *